United States Patent [19]

Haber et al.

[11] Patent Number: 5,052,403
[45] Date of Patent: Oct. 1, 1991

[54] SELF-CONTAINED, SAFETY BLOOD COLLECTION SYSTEM

[75] Inventors: Terry M. Haber, El Toro; Clark B. Foster, Laguna Niguel; William H. Smedley, Lake Elsinore, all of Calif.

[73] Assignee: Habley Medical Technology Corporation, Laguna Hills, Calif.

[21] Appl. No.: 458,887

[22] Filed: Dec. 29, 1989

[51] Int. Cl.$^5$ .............................................. A61B 5/00
[52] U.S. Cl. ..................................................... 128/765
[58] Field of Search ............... 128/760, 763, 765, 770; 604/192-199

[56] References Cited

U.S. PATENT DOCUMENTS

| | | | |
|---|---|---|---|
| 3,577,980 | 5/1971 | Cohen | 128/765 |
| 3,753,432 | 8/1973 | Guerra | 128/765 |
| 4,890,627 | 1/1990 | Haber et al. | 128/765 |
| 4,900,310 | 2/1990 | Ogle | 604/198 |

Primary Examiner—Max Hindenburg
Attorney, Agent, or Firm—Hawes & Fischer

[57] ABSTRACT

A self-contained, safety blood collection system comprising a shatter-resistent blood collection tube in which a vacuum may be manually established and in which a blood sample, or the like, may be collected by way of a retractable, single ended needle cannula. A piston is relocated from an as-packaged, distal position within the blood collection tube to a proximal position so as to evacuate the tube, whereby the tube is automatically infused with blood under the influence of suction. A controllable fluid valve is formed in an elastomeric stopper, and the stopper is located within the distal end of the blood collection tube, such that the volume and rate at which blood is collected within the tube can be selectively varied. An auxiliary fluid port is formed in the stopper through which successive blood samples may be collected in additional blood collection systems from the same veni puncture.

21 Claims, 4 Drawing Sheets

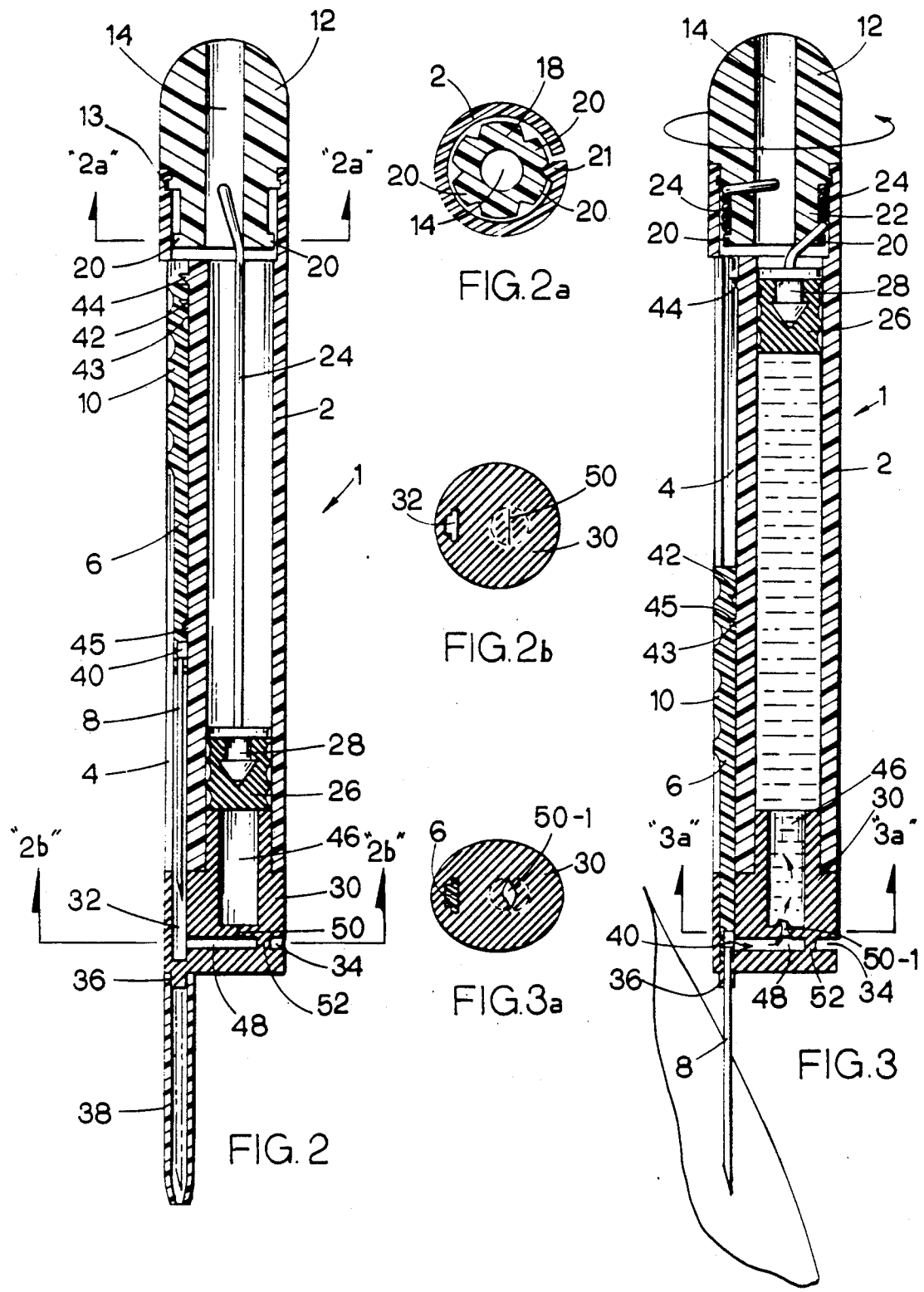

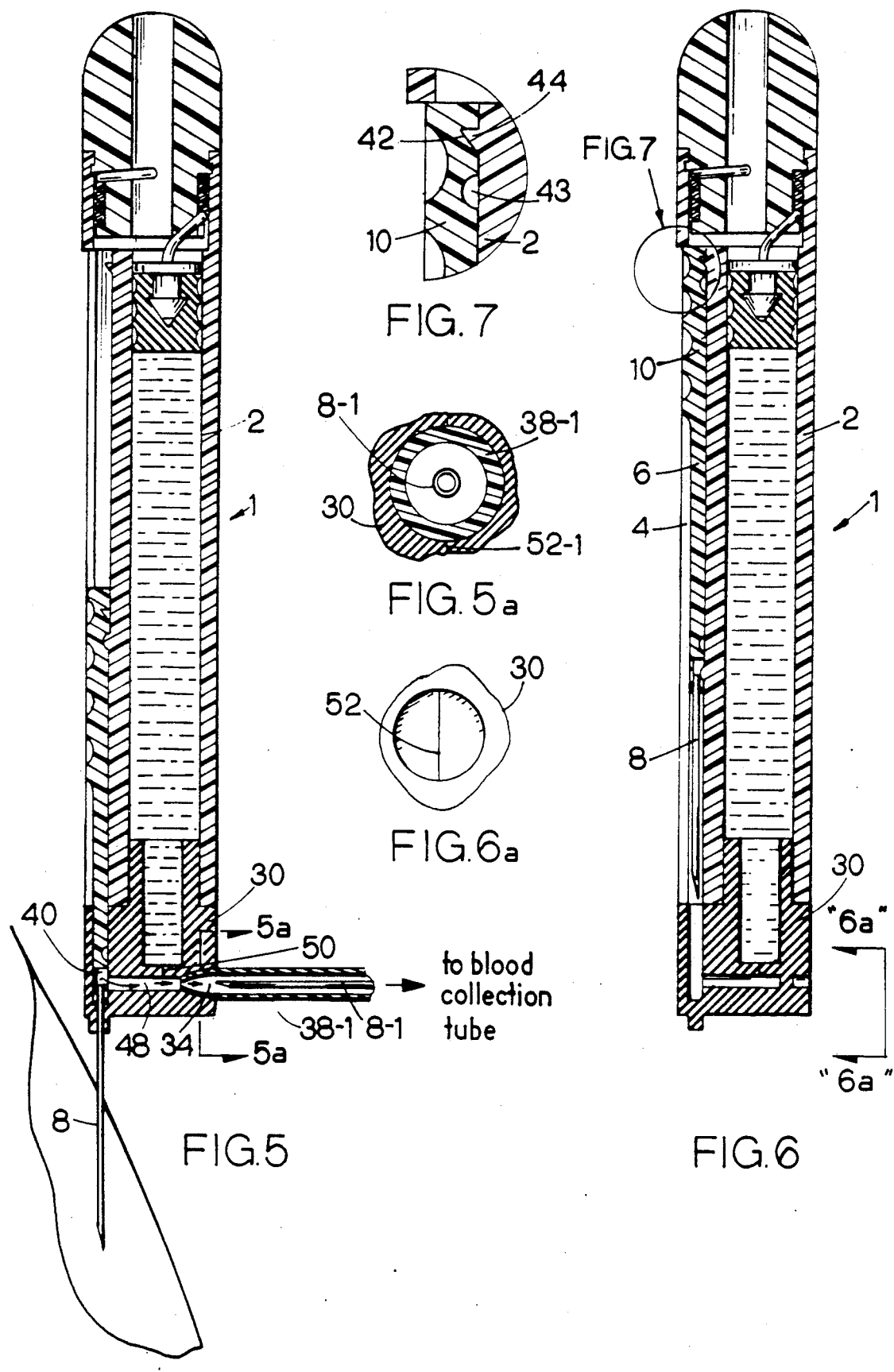

SELF-CONTAINED, SAFETY BLOOD COLLECTION SYSTEM

BACKGROUND OF THE INVENTION

1. FIELD OF THE INVENTION

This invention relates to a self-contained, safety blood collection system comprising a shatter-resistant blood collection tube in which a vacuum is manually and selectively established so that the tube is automatically infused with a blood sample, under the influence of suction, by way of an associated retractable needle cannula.

2. BACKGROUND ART

The practice of vacuum tube phlebotomy is a well-known art. That is to say, it is well known to use a syringe apparatus including a separate double ended needle cannula, a blood collection tube holder and an evacuated blood collection tube or vial into which a blood sample can be drawn from a patient. The typical blood collection tube has a self-sealing stopper located at an open end thereof to preserve a vacuum that has been mechanically established at the interior of the tube. One end of the double ended needle cannula penetrates the stopper and the other end makes a veni puncture through the patient's tissue to permit the tube to be automatically infused with a sample of the patient's blood.

However, the conventional blood collection tube is commonly evacuated by an array of often complex handling and air evacuating equipment. The cost of using and maintaining such handling and vacuum producing equipment significantly contributes to the overall cost of the blood collection system. Moreover, the requirement for a separate double ended needle cannula, blood collection tube and blood collection tube holder further increases the total cost of the system. What is still more, when a conventional blood collection tube is stored for a long period of time prior to use, the rubber stopper may erode such that the vacuum-sterile environment of the tube may be jeopardized.

The conventional blood collection tube is usually made of glass. Such tubes have been known to shatter when dropped or otherwise impacted by a shock transmitting force. Consequently, the possibility exists that a blood precautionary sample therewithin may leak or splatter and, consequently, spread a contagious, and possibly life threatening, disease, such as AIDS, or the like.

U.S. Pat. No. 4,890,627 issued Jan. 2, 1990 and assigned to the assignee of the present patent application discloses a manually evacuated suction tube that is manufactured from a shatter-resistant material.

SUMMARY OF THE INVENTION

In general terms, a self-contained blood collection system is disclosed in which a sample of a bodily fluid, such as blood, or the like, may be easily, efficiently and safely collected. The blood collection system includes a shatter resistant blood collection tube in which a vacuum is manually established so that a blood sample can be collected therein under the influence of suction. An elastomeric stopper is located at the distal end of the blood collection tube to seal said distal end. A rotatable vacuum inducing knob is located at the proximal end of the blood collection tube. A ratchet, having a series of teeth extending around the periphery thereof, is connected to and rotatable with the vacuum inducing knob.

A piston is initially located at a relatively distal position within the blood collection tube, and a pair of non-extensible tethers are connected between the piston and the vacuum inducing knob, such that a rotation of said knob causes the tethers to be wound therearound, whereby to correspondingly cause a proximal relocation of the piston through the blood collection tube and the expulsion of air therefrom for establishing a vacuum therein.

A relatively low cost, single ended needle cannula is attached to a needle hub that is adapted to slide reciprocally through an axially extending track formed in the blood collection tube between a retracted position, where the cannula is shielded in the track before and after use to avoid an accidental needle stick and the spread of a contagious disease, and an axially extended position, where the sharp distal tip of the cannula is advanced to make a veni puncture through the patient's tissue. The blunt proximal end of the cannula communicates with the blood collection tube through a normally closed primary fluid valve (i.e. slit) that is formed in the elastomeric stopper and located between the cannula and the blood collection tube. Compressive forces are selectively applied to deform the elastomeric stopper and thereby open the slit thereof so that the volume and rate at which the blood collection tube is infused can be controllably varied.

An auxiliary fluid port is also formed in the stopper so as to communicate with the needle cannula by way of a normally closed secondary fluid valve (i.e. slit). A fluid conveying sleeve is received in the fluid port and passed through the sleeve to thereby open the sleeve and complete a fluid path between the cannula and the sleeve. Accordingly, successive blood samples may be collected in additional collection systems from a single veni puncture made by the needle cannula and delivered by the fluid conveying sleeve.

BRIEF DESCRIPTION OF THE DRAWINGS

FIG. 2 is a cross-section of the blood collection system of FIG. 1 in the assembled, as-packaged configuration;

FIG. 2a is a cross-section taken along lines 2a—2a of FIG. 2;

FIG. 2b is a cross-section taken along lines 2b—2b of FIG. 2;

FIG. 3 is a cross-section of the blood collection system being infused with a blood sample by way of an axially extended needle cannula;

FIG. 3a is a cross-section taken along lines 3a—3a of FIG. 3;

FIG. 5 is a cross-section of the blood collection system of FIG. 3 interfaced with another blood collection system so that additional blood samples can be collected from a single veni puncture;

FIG. 5a is a cross-section taken along lines 5a—5a of FIG. 5;

FIG. 6 is a cross-section of the blood collection system after the last blood sample has been collected and the needle cannula thereof has been safely relocated to a retracted position;

FIG. 6a is a partial side view taken along lines 6a—6a of FIG. 6; and

FIG. 7 is an enlarged detail taken from FIG. 6.

DESCRIPTION OF THE PREFERRED EMBODIMENT

Figure 1:
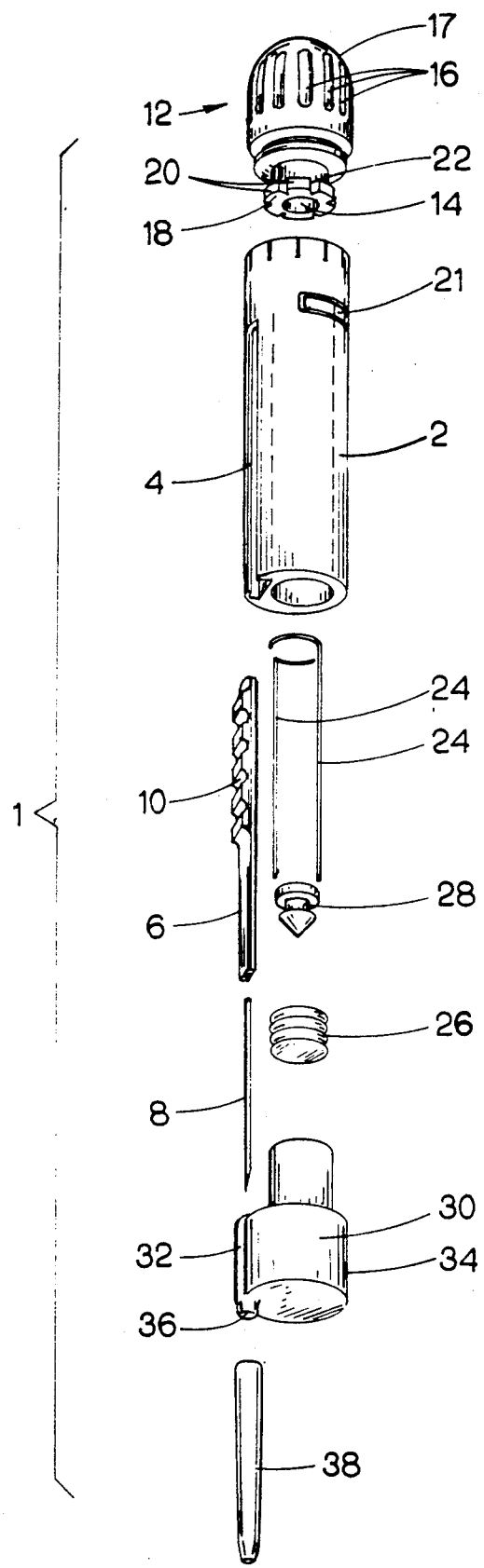
FIG. 1 is an exploded view of the safety blood collection system which forms the present invention.

The self-contained, safety blood collection system 1 which forms the present invention is now described while referring to the drawings, where FIG. 1 shows an exploded view of the blood collection system. Blood collection system 1 includes a hollow, cylindrical blood collection tube 2 having open proximal and distal ends and being preferably formed form a non-breakable, shatter resistant material, such as plastic, or the like. A narrow, longitudinally extending track 4 is molded into blood collection tube 2 within which to receive a slidable needle hub 6. Needle hub 6, to which a low cost single ended needle cannula 8 is connected (e g. molded or epoxied), is coextensively formed with a slide member 10. Slide member 10 is received within and slidable reciprocally through the track 4 in tube 2 for relocating hub 6 and the cannula 8 connected thereto between a retracted position (of FIG. 2), at which the cannula is safely shielded to avoid an accidental needle stick, and an axially extended position (of FIG. 3), at which to make a veni puncture through a patient's tissue to collect one or more samples of the patient's blood.

Located at the open proximal end of blood collection tube 2 is a rotatable vacuum inducing knob 12. Vacuum inducing knob 12 includes a central exhaust passage 14 through which air is expulsed in order to evacuate the blood collection tube 2 (in a manner to be described in greater detail hereinafter). The knob 12 includes a head portion 17 at one end thereof in which a plurality of parallel aligned gripping serrations 16 are formed. At the opposite end of knob 12 is a ratchet 18 having a plurality of teeth 20 extending around the periphery thereof. In the assembled configuration of FIG. 2, the teeth 20 of ratchet 18 cooperate with a resilient detent 21 that is coextensively formed with and extended inwardly from the proximal end of tube 2. Located between the head 17 and ratchet 18 of vacuum inducing knob 12 is a relatively narrow neck 22, around which a pair of piston tethers 24 are to be wound for relocating a vacuum inducing piston 26 proximally through blood collection tube 2 and thereby establishing a vacuum therewithin.

Piston tethers 24 are preferably formed from a nonextensible filament material to resist elongation and breaking. One end of each tether 24 is attached (e.g. by sonic welding) to a rigid piston supporting plug 28. Plug 28 carries the vacuum inducing piston 26 thereon. The opposite ends of tethers 24 are affixed (e.g. adhesively bonded) to the vacuum inducing knob 12 at the neck 22 thereof, such that tethers 24 are rotatable around said neck 22 when the head 17 of knob 12 is manually grasped and rotated.

Located within the open distal end of blood collection tube 2 is a removable stopper 30 which is preferably formed from an elastomeric material having a characteristic spring-like memory. As will be described when referring to FIG. 2, stopper 30 includes an integral, manually controllable valve by which the volume and rate at which blood is received within blood collection tube 2 via needle cannula 8 can be selectively varied. Stopper 30 has a narrow channel 32 extending longitudinally through the interior thereof which is axially aligned with the track 4 in blood collection tube 2. In the assembled configuration of FIG. 2, the track 4 and channel 32 form a longitudinally extending path for guiding needle cannula 8 between the retracted and axially extended positions. An auxiliary fluid port 34 is formed in stopper 30, the advantage of which will be described when referring to FIG. 5.

A terminal 36 is molded into the forward end of stopper 30 to be axially aligned with the channel 32 thereof. Terminal 36 is dimensioned so that an open ended needle shielding and blood conveying sleeve 38 can be detachably connected to stopper 30 at terminal 36. As is best shown in FIG. 2, the sleeve 38 is carried by the stopper 30 so as to receive therewithin and shield the needle cannula 8 and thereby prevent an accidental needle stick prior to use when said cannula is advanced to the axially extended position to make a veni puncture. In the alternative, and as is shown in FIG. 5, the sleeve 38 from a second blood collection system can be fluidically coupled to the axially extended cannula 8 at auxiliary fluid port 34 so that one or more additional blood samples may be collected from a single veni puncture.

FIG. 2 of the drawings shows the blood collection system 1 of the present invention in the assembled, as-packaged configuration. More particularly, the rotatable vacuum inducing knob 12 includes a flange which is snap-fit within and supported for rotation by a peripheral groove 13 that is formed around the proximal end of blood collection tube 2 so that the exhaust passage 14 of knob 12 communicates with the interior of tube 2 and the ratchet (18 of FIG. 1) is received through and coaxially aligned with said proximal end. The stopper 30 is located within the distal end of blood collection tube 2 so as to form a fluid tight seal therewith. The slide member 10, to which needle hub 6 is connected, is shown, in the as-packaged configuration, located proximally within the track 4 of blood collection tube 2, such that needle cannula 8 is disposed in the retracted position to avoid an accidental needle stick prior to use. It may also be noted that the sharp, distal tip of cannula 8 is located within the interior channel 32 of stopper 30 to preserve the sterility of cannula 8. The needle cannula 8 is connected to needle hub 6, such that the blunt proximal end of said cannula communicates with a hollow pocket 40 that is formed in said hub. In the as-packaged configuration, the needle shielding and blood conveying sleeve 38 is releasably attached to the stopper 3 at the terminal 38 thereof, such that sleeve 38 is in axial alignment with the track 4 and channel 32 to receive the needle cannula (shown in phantom) therewithin when said cannula is advanced to the axially extended position prior to making a veni puncture.

The slide member 10 includes first and second recesses 42 and 43 formed therein and located adjacent the blood collection tube 2. Molded into and projecting outwardly from the tube 2 are first and second catches 44 and 45. The first and second catches 44 and 45 are axially spaced from one another along blood collection tube 2 and particularly shaped to be received within respective recesses 42 and 43 of slide member 6 depending upon whether the needle cannula 8 has been advanced, by needle hub 6 and slide member 10, to the axially extended position at which to make a veni puncture, or withdrawn to the retracted position, after one or more blood samples have been collected.

The stopper 30 includes a longitudinally extending fluid chamber 46 and a laterally extending fluid inlet passage 48 which are separated from one another by a primary fluid valve 50. Primary fluid valve 50 comprises a slit which extends between chamber 46 and inlet passage 48 and which, in the as-packaged configuration, is normally closed to prevent the flow of blood from passage 48 to chamber 46. Stopper 30 also includes a secondary fluid valve 52 which extends between fluid inlet passage 48 and auxiliary fluid port 34. Secondary fluid valve 52 comprises a slit which, in the as-packaged configuration, is normally closed to prevent fluid flow from inlet passage 48 to fluid port 34.

In the as-packaged configuration of FIG. 2, the piston 26 is located adjacent the distal end of blood collection tube 2, and the piston tethers 24 (only one of which being visible) are fully and longitudinally extended through tube 2 between piston supporting plug 28, to which the piston 26 is attached, and the vacuum inducing knob 12 at the proximal end of tube 2. The ratchet 18 (best shown in FIG. 2a) of knob 12 is received through the proximal end of blood collection tube 2, so that the resilient ratchet control detent 21 which projects inwardly of tube 2 is received between a pair of adjacent teeth 20 of ratchet 18 (also best shown in FIG. 2a) to control the direction of rotation of said ratchet, in a manner that will soon be described.

The operation of the safety blood collection system 1 of the present invention is described while referring to FIGS. 3-6 of the drawings. In FIG. 3, the piston 26 is moved proximally through blood collection tube 2 to evacuate said tube, and the needle cannula 8 is advanced to the axially extended position to make a veni puncture so that a sample of the patient's blood can be easily and efficiently collected at the interior of tube 2. More particularly, the health care worker initially rotates the vacuum inducing knob 12. Inasmuch as one end of each of the tethers 24 is attached to vacuum inducing knob 12, a rotation of knob 12 causes tethers 24 to be wound up around the neck 22 thereof. Since the opposite end of each of the tethers 24 is attached to piston supporting plug 28, the winding up of tethers 24 around the neck 22 of knob 12 causes a corresponding proximal relocation of plug 28 and the piston 26 connected thereto through blood collection tube 2. Thus, it may be observed that a rotational movement of vacuum inducing knob 12 is translated into a linear and proximal movement of piston 26 through blood collection tube 2 by means of tethers 24. The proximal relocation of piston 26 through tube 2 expulses air trapped within tube 2 to the atmosphere via the exhaust passage 14 of knob 12, whereby to create a vacuum within said tube. With piston located at the proximal end of blood collection tube 2, said tube is completely sealed and the vacuum therewithin preserved.

As vacuum inducing knob 12 is rotated, the ratchet 18 (of FIG. 2a) which is disposed within the proximal end of blood collection tube 2, is correspondingly rotated relative to the ratchet control detent 21 (also of FIG. 2a) of blood collection tube 2. Hence, the resilient ratchet control detent 21 will be continuously relocated between successive pairs of the ratchet teeth 20. The receipt of ratchet control detent 21 between a pair of teeth 20 of ratchet 18 will prevent the unintended counter-rotation of said ratchet and the unwinding of tethers 24 from the neck 22 of vacuum inducing knob 12 in the event that the rotation of knob 12 is interrupted. Thus, the tethers 24 will, at all times, remain in a relatively taut condition and in a longitudinally extended alignment between knob 12 and piston supporting plug 28 to assure the smooth and continuous proximal relocation of piston 26 through blood collection tube 2 for establishing a vacuum therein in response to the rotation of vacuum inducing knob 12.

In FIG. 3 of the drawings, the needle cannula 8 is advanced to the axially extended position by pushing slide member 10 in a distal direction, whereby to advance needle hub 6 through the track 4 in blood collection tube 2 and into the channel (designated 32 in FIG. 2) of stopper 30, such that the cannula pierces and moves outwardly through the terminal 36 of said stopper. The cannula 8 is automatically and releasably retained in the axially extended position, inasmuch as the recess 43 of slide member 10 is moved into removable receipt of the correspondingly sized catch 45 of blood collection tube 2 to prevent an inadvertent distal relocation of needle hub 6 relative to tube 2. With cannula 8 advanced to the axially extended position, the pocket 40 of needle hub 6, within which the proximal end of cannula 8 is disposed, is aligned with the fluid inlet passage 48 of stopper 30.

The shielding sleeve (designated 38 in FIG. 2) is now removed from needle cannula 8 and the cannula is used to make a veni puncture through the patient's tissue. As previously disclosed when referring to FIG. 2, the primary fluid valve (i.e. slit) 50 of stopper 30 is initially in a normally closed configuration (best illustrated in FIG. 2b) to block the flow of blood from the fluid inlet passage 48 to the fluid chamber 46 of stopper 30. However, primary fluid valve 50 may be manually opened to vary both the volume and rate at which blood flows between inlet passage 48 and chamber 46 of stopper 30 for receipt, under suction, within the evacuated blood collection tube 2.

Figure 4:
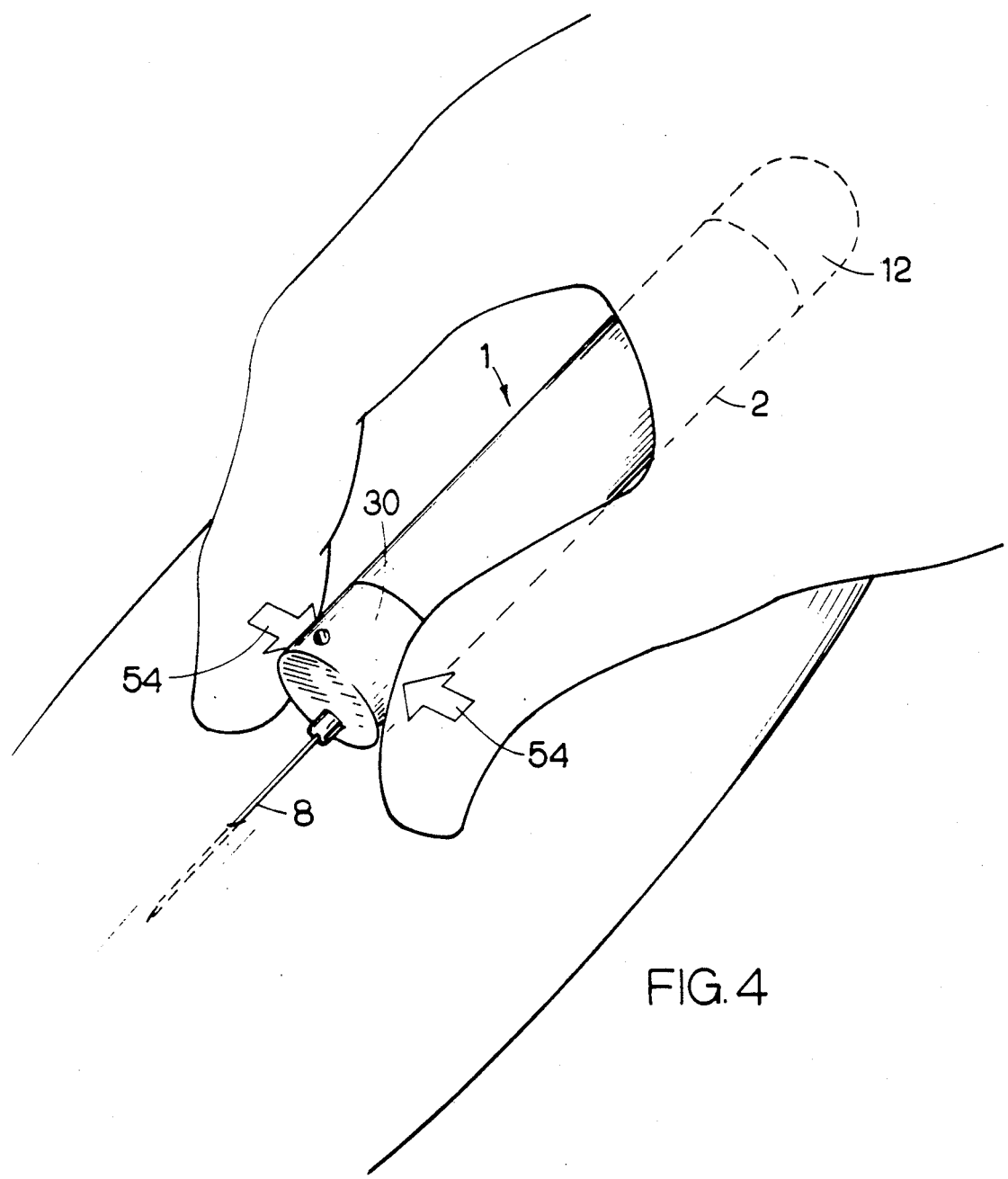
FIG. 4 is a perspective view of the blood collection system of FIG. 3 making a veni puncture and being infused with a blood sample.

That is to say, and referring concurrently to FIGS. 3 and 4, the health care worker uses his thumb and forefinger to apply equal and opposite compressive forces (in the directions indicated by the reference arrows 54 of FIG. 4) which are oriented in axial alignment with the slit of primary valve 50. Accordingly, the fluid valve 50 of elastomeric stopper 30 is slightly deformed, whereby to cause the slit (designated 50-1 and best illustrated in FIG. 3a) to open and thereby complete a continuous fluid path between needle cannula 8 and the evacuated interior of blood collection tube 2 via the pocket 40 of needle hub 6 (with which the proximal end of cannula 8 communicates), fluid inlet passage 48, the open fluid valve 50-1 and the fluid chamber 46 of stopper 38. Hence, blood collection tube 2 is automatically infused with a sample of the patient's blood under the influence of suction.

However, and as a distinct advantage of the blood collection system 1 of the present invention, the health care worker may selectively regulate the volume and rate at which the patient's blood fills blood collection tube 2 by adjusting the magnitude of the compressive forces 54 that are applied to deform stopper 30, whereby to correspondingly vary the width of the slit of the primary fluid valve between completely closed (designated 50 in FIG. 2b) and fully open (designated 50-1 in FIG. 3a). Once the blood collection tube 2 is filled with a desired volume of blood, the health care worker removes his fingers from stopper 30 so as to discontinue the application of force thereto and permit primary fluid valve 50 to automatically return (by the spring-like memory of the elastomeric material thereof) to its normally closed position (of FIG. 2b) to isolate the blood sample collected in tube 2 from cannula 8.

As another important advantage of the present invention, and referring to FIG. 5 of the drawings, one or more additional samples of the patient's blood may be taken from the same veni puncture subsequent to the initial sample that was collected in blood collection tube 2 and described when referring to FIGS. 3 and 4. More particularly, with the primary fluid valve 50 closed and the blood sample in blood collection tube 2 isolated from needle cannula 8, the health care worker inserts the open ended needle shielding and blood conveying sleeve 38-1 that is associated with a second blood collection system (which is not shown in FIG. 5 but is identical to that previously described herein) into the auxiliary fluid port 34 of stopper 30 of the illustrated blood collection system 1. As previously disclosed, the secondary fluid valve (i.e. slit) 52 between fluid inlet passage 48 and auxiliary fluid port 34 is normally closed (best illustrated in FIG. 6a) to prevent the flow of blood therebetween. However, the blood conveying sleeve 38-1 which is inserted into auxiliary fluid port 34 also extends through the secondary fluid valve 52, whereby the slit thereof is opened (designated 52-1 in FIG. 5a). Accordingly, a continuous fluid path is completed between the needle cannula 8 of blood collection system 1 and the needle cannula 8-1 of the second blood collection system (not shown) via pocket 40, fluid inlet passage 48, secondary fluid valve 52-1 and blood conveying sleeve 38-1. Hence, the blood collection tube of the second blood collection system is automatically infused with another sample of the patient's blood, under the influence of suction, in the same manner that blood collection tube 2 of blood collection system 1 was earlier infused.

Once the additional blood sample has been taken, the health care worker removes the blood conveying sleeve 38-1 from the auxiliary fluid port 34 of stopper 30. Hence, the slit of secondary fluid valve 52 automatically returns (by the spring-like memory of the elastomeric material of stopper 30) to its normally closed position (of FIG. 6a) to isolate the newly collected blood sample from needle cannula 8. The aforementioned process by which additional samples of the patient's blood are collected in the respective blood collection tubes of additional blood collection systems may be repeated as many times as is needed, according to medical testing requirements. However, only a single veni puncture need be made such that the needle cannula 8 of blood collection system 1 is not removed from the patient's tissue until the final blood sample has been taken.

After the final blood sample has been collected, and referring now to FIG. 6 of the drawings, the needle cannula 8 of blood collection system 1 is removed from the patient's tissue and returned to and locked in the retracted position so as to avoid an accidental needle stick. More particularly, the health care worker applies a pulling force to slide member 10, whereby to cause needle hub 6 and the cannula 8 attached thereto to slide proximally through the track 4 in blood collection tube 2. Thus, the sharp distal tip of cannula 8 will be surrounded by and rendered inaccessible within track 4. Moreover, the slide member 10 is locked in the retracted position to prevent a return of cannula 8 to the axially extended position at which the veni puncture was made.

More particularly, and referring concurrently to FIGS. 6 and 7, slide member 1 is relocated proximally through the track 4 of blood collection tube 2 until the catch 44 at the proximal end of tube 2 is received within the correspondingly shaped recess 42 is slide member 10. The catch 44 and recess 44 are provided with suitable (e.g. ramp-like) shapes which permit the proximal relocation of slide member 10 relative to tube 2. However, with catch 44 received in recess 42, the distal relocation of slide member 10 relative to tube 2 is blocked. Hence, slide member 10 will be locked at a relatively proximal location along blood collection tube 2, while needle cannula 8 is retained within track 4 in the retracted position.

The blood collection system 1 may now be safely handled and transported to a medical test facility. Access to the patient's blood is easily obtained from blood collection tube 2 for testing and evaluation purposes by either removing the stopper 30 from the distal end of tube 2 or by inserting a relatively long needle probe (not shown) through said stopper. When sufficient blood has been removed from tube 2, the blood collection system 1 may be discarded. However, the health care worker is not required to handle or destroy the needle cannula 8, and said cannula remains surrounded by track 4 to avoid the possibility of an accidental needle stick and the spread of contagious disease.

By virtue of the presently disclosed self-contained, safety blood collection system 1, the need for and corresponding cost of a separate blood collection tube holder and double ended needle cannula, which are common to conventional blood collection systems, are eliminated That is, blood collection system 1 has an integrated collection tube holder and single ended needle cannula, and the built-in needle shielding and anti-stick safety features eliminate the need for a separate blood collection tube holder. The volume and rate at which a blood sample is collected by system 1 is manually and selectively variable to meet health care requirements. Moreover, the system permits multiple blood samples to be obtained from a single veni puncture while offering continued needle stick protection. Inasmuch as blood collection tube is manufactured from a shatter-resistant material, the possibility of spreading a contagious disease in the event that the tube is dropped while carrying a blood precautionary sample is advantageously reduced. Since the blood collection tube 2 is evacuated only at the time of use, there is less opportunity for the seals thereof to leak as a consequence of age, whereby the blood collection system 1 of the present invention will have a nearly unlimited shelf life.

It will be apparent that while a preferred embodiment of the invention has been shown and described, various modifications and changes may be made without departing from the true spirit and scope of the invention. For example, while the blood collection system of the present invention has been described as having particular application for collecting a blood sample, it is to be understood that said system has other applications including, but not limited to, treating a snake bite, draining a cyst, draining a wound, taking a biopsy, or esophageal aspiration.

Having set forth a preferred embodiment of the invention, what is claimed is:

1. A fluid collection system for collecting a sample of a bodily fluid and comprising:
   a fluid collection tube having distal and proximal ends and in which a vacuum is to be established so that the fluid sample is collected within said tube under the influence of suction;
   stopper means located at the distal end of said fluid collection tube to seal said distal end;

a needle cannula to penetrate the tissue of a patient at a first end and to communicate fluidically with said fluid collection tube at the opposite end thereof;

rotatable knob means located at the proximal end of said fluid collection tube;

piston means located at a relatively distal position within said fluid collection tube between said stopper means and said rotatable knob means; and linking means extending between said piston means and said rotatable knob means, such that a rotation of said knob means causes said linking means to be pulled axially through said fluid collection tube and said piston means to be relocated proximally through said tube for expulsing air therefrom and establishing a vacuum therein.

2. The fluid collection system recited in claim 1, wherein said rotatable knob means has an exhaust passage extending between the interior of said fluid collection tube and the atmosphere, such that air from said tube is expulsed through said exhaust passage when said piston means is relocated proximally through said tube.

3. The fluid collection system recited in claim 1, wherein said linking means comprises at least one relatively non-extensible tether that is connected from said piston means to said rotatable knob means, such that a rotation of said knob means causes said tether to wind up around said knob means for correspondingly pulling said piston means through and establishing the vacuum in said fluid collection tube.

4. The fluid collection system recited in claim 3, further comprising ratchet means located within said fluid collection tube, said ratchet means connected to and rotated with said rotatable knob means; and detent means projecting inwardly from said fluid collection tube and cooperating with said ratchet means to prevent the counter-rotation of said knob means and an unwinding of said tether therefrom.

5. The fluid collection system recited in claim 1, further comprising means by which said needle cannula is moved axially and reciprocally relative to said fluid collection tube between a retracted position, at which said cannula is shielded to prevent an accidental needle stick, and an extended position, at which said cannula is advanced so as to be able to penetrate the patient's tissue.

6. The fluid collection system recited in claim 5, wherein the means by which said needle cannula is movable includes a track extending axially along said fluid collection tube and a needle hub connected to said cannula and slidable reciprocally through said track so that said cannula is relocated between the retracted and extended positions.

7. The fluid collection system recited in claim 6, further comprising means to engage said needle hub to prevent both the displacement of said hub through said track and the relocation of said needle cannula to the extended position after a fluid sample has been collected within said fluid collection tube and said cannula has been relocated to the retracted position.

8. The fluid collection system recited in claim 1, further comprising valve means located between and in fluid communication with said needle cannula and said fluid collection tube so that the fluid collected in said tube via said cannula can be selectively controlled.

9. The fluid collection system recited in claim 8, wherein said stopper means is formed from an elastomeric material having a spring-like resiliency and said valve means includes a normally closed slit formed in said stopper means, said slit being responsive to a compressive force that is applied to said stopper means in axial alignment with said slit, such that the shape of said stopper means is deformed and said slit is opened to permit the passage of fluid from said cannula to said fluid collection tube.

10. The fluid collection system recited in claim 9, further comprising a fluid inlet passage formed in said stopper means and located between said needle cannula and said slit, such that fluid is conveyed from said cannula to said slit by way of said fluid inlet passage.

11. The fluid collection system recited in claim 1, further comprising a fluid exit port formed in said stopper means; and normally closed valve means located between and in fluid communication with said needle cannula and said fluid exit port, such that a fluid path is established from said cannula to said port when said valve means is opened.

12. The fluid collection system recited in claim 11, wherein said stopper means is formed from an elastomeric material having a spring-like resiliency and said valve means includes a normally closed slit, said slit being opened when a fluid conveying means is inserted into said exit port and through said slit, so as to complete a fluid path from said needle cannula to the fluid conveying means that has been inserted into said port and through said slit.

13. A fluid collection system for collection a sample of bodily fluid and comprising:

a fluid collection tube having distal and proximal ends and in which a vacuum is to be established so that the fluid sample is collected within said tube under the influence of suction;

stopper means located at the distal end of said fluid collection tube to seal said distal end;

closure means located at the proximal end of said fluid collection tube;

piston means located at a relatively distal position within said fluid collection tube between said stopper means and said closure means;

means by which to move said piston means axially and proximally through said fluid collection tube for expulsing air therefrom and establishing a vacuum therein;

a needle cannula to penetrate the tissue of a patient at a first end and to communicate fluidically with said fluid collection tube at the opposite end thereof; and means by which said cannula is moved axially and reciprocally relative to said fluid collection tube between a retracted position, at which said cannula is shielded to prevent an accidental needle stick, and an extended position, at which said cannula is advanced so as to be able to penetrate the patient's tissue.

14. The fluid collection system recited in claim 13, wherein the means by which said needle cannula is movable includes a track extending axially along said fluid collection tube and a needle hub connected to said cannula and slidable reciprocally through said track so that said cannula is relocated between the retracted and extended positions.

15. The fluid collection system recited in claim 14, further comprising means to engage said needle hub to prevent both the displacement of said hub through said track and the relocation of said needle cannula to the extended position after a fluid sample bas been collected within said fluid collection tube and said cannula has been relocated to the retracted position.

16. The blood collection system recited in claim 13, wherein said closure means at the proximal end of said fluid collection tube is a rotatable knob, said system further comprising linking means connected between said piston means and said rotatable knob, such that a rotation of said knob causes said linking means to wind up around said knob for correspondingly pulling said piston means axially and proximally through said tube for expulsing air therefrom and establishing a vacuum therein.

17. The fluid collection system recited in claim 16, wherein said rotatable knob has an exhaust passage extending between the interior of said fluid collection tube and the atmosphere, such that air from said tube is expulsed through said exhaust passage when said piston means is relocated proximally through said tube.

18. The fluid collection system recited in claim 16, further comprising means located at the interior of said fluid collection tube to engage said rotatable knob so as to prevent a counter-rotation of said knob and an unwinding of said linking means therefrom.

19. The fluid collection system recited in claim 16, further comprising ratchet means located within said fluid collection tube, said ratchet means connected to and rotated with said rotatable knob; and detent means projecting inwardly from said fluid collection tube and cooperating with said ratchet means to prevent the counter-rotation of said knob and an unwinding of said linking means therefrom.

20. The fluid collection system recited in claim 13, further comprising normally closed valve means formed in said stopper means and communicating with said fluid collection tube, said valve means also communicating with said needle cannula when said cannula is advanced to the extended position to thereby establish a fluid path between said cannula and said tube when said valve means is opened and control the fluid which is supplied to said tube by way of said cannula.

21. The fluid collection system recited in claim 20, wherein said stopper means is formed from an elastomeric material having a spring-like resiliency and said valve means includes a normally closed slit formed in said stopper means, said slit being responsive to a compressive force that is applied to said stopper means in axial alignment with said slit, such that the shape of said stopper means is deformed and said slit is opened to permit the passage of fluid from said cannula to said fluid collection tube.

* * * * *